US008379296B2

(12) United States Patent
Schunemann et al.

(10) Patent No.: US 8,379,296 B2
(45) Date of Patent: Feb. 19, 2013

(54) NONLINEAR OPTICAL CDSIP2 CRYSTAL AND PRODUCING METHOD AND DEVICES THEREFROM

(75) Inventors: Peter G Schunemann, Hollis, NH (US); Kevin T Zawilski, Arlington, MA (US)

(73) Assignee: BAE Systems Information and Electronic Systems Integration Inc., Nashua, NH (US)

( * ) Notice: Subject to any disclaimer, the term of this patent is extended or adjusted under 35 U.S.C. 154(b) by 300 days.

(21) Appl. No.: 12/809,103

(22) PCT Filed: Oct. 23, 2009

(86) PCT No.: PCT/US2009/061786
§ 371 (c)(1),
(2), (4) Date: Jun. 18, 2010

(87) PCT Pub. No.: WO2010/082968
PCT Pub. Date: Jul. 22, 2010

(65) Prior Publication Data
US 2011/0054451 A1     Mar. 3, 2011

Related U.S. Application Data

(60) Provisional application No. 61/107,876, filed on Oct. 23, 2008.

(51) Int. Cl.
*G02F 2/02* (2006.01)
*G02F 1/35* (2006.01)
(52) U.S. Cl. ........... 359/328; 359/326; 372/22; 385/122
(58) Field of Classification Search .......... 359/326–332; 385/122; 372/21–22
See application file for complete search history.

(56) References Cited

U.S. PATENT DOCUMENTS

| 4,649,544 | A | 3/1987 | Haas et al. |
| 5,038,352 | A | 8/1991 | Lenth et al. |
| 5,611,856 | A | 3/1997 | Schunemann et al. |
| 5,768,302 | A | 6/1998 | Wallace et al. |
| 6,358,243 | B1 | 3/2002 | Esterowitz et al. |
| RE38,339 | E | 12/2003 | Ukita et al. |
| 6,942,728 | B2 | 9/2005 | Caillat et al. |
| 2011/0058248 | A1* | 3/2011 | Vodopyanov et al. ........ 359/330 |
| 2011/0064096 | A1* | 3/2011 | Shah et al. ........................ 372/6 |

OTHER PUBLICATIONS

PCT Search Report dated Jun. 24, 2010 of Patent Application No. PCT/US2009/061786 filed Oct. 23, 2009.
S.C. Abrahams and J.L. Bernstein, J. Chem. Phys. vol. 55, p. 796 (1971).

(Continued)

*Primary Examiner* — Daniel Petkovsek
(74) *Attorney, Agent, or Firm* — Maine Cernota & Rardin; Douglas P. Burum; Daniel J. Long

(57) ABSTRACT

$CdSiP_2$ crystals with sizes and optical quality suitable for use as nonlinear optical devices are disclosed, as well as NLO devices based thereupon. A method of growing the crystals by directional solidification from a stoichiometric melt is also disclosed. The disclosed NLO crystals have a higher nonlinear coefficient than prior art crystals that can be pumped by solid state lasers, and are particularly useful for frequency shifting 1.06 μm, 1.55 μm, and 2 μm lasers to wavelengths between 2 μm and 10 μm. Due to the high thermal conductivity and low losses of the claimed $CdSiP_2$ crystals, average output power can exceed 10 W without severe thermal lensing. A 6.45 μm laser source for use as a medical laser scalpel is also disclosed, in which a $CdSiP_2$ crystal is configured for non-critical phase matching, pumped by a 1064 nm Nd:YAG laser, and temperature-tuned to produce output at 6.45 μm.

15 Claims, 6 Drawing Sheets

OTHER PUBLICATIONS

N. Itoh, T. Fujinaga, and T. Nakau, "Birefringence in CdSiP2," Jap. J. Appl. Phys. 17,951-2, (1978).

E. Buehler and J.H. Wernick, Journal of Crystal Growth 8, 324 (1971).

M. J. Weber (ed.) CRC Handbook of Laser Science and Technology, vol. 3., (CRC Press, Boca Raton, Florida, 1986).

Nature 371, 416-419, Sep. 29, 1994.

K. Zawilski and P. Schunemann, New nonlinear optical crystal for mid-IR OPOs: CdSiP2 (2008).

K. Zawilski and P. Schunemann, New mid-IR nonlinear optical crystal: CdSiP2 (2008).

K. Zawilski and P. Schunemann, Journal of Crystal Growth, vol. 312, Issue 8, Apr. 1, 2010.

* cited by examiner

NONLINEAR OPTICAL CDSIP2 CRYSTAL AND PRODUCING METHOD AND DEVICES THEREFROM

RELATED APPLICATIONS

This application claims the benefit of U.S. Provisional Application No. 61/107,876, filed Oct. 23, 2008, incorporated herein by reference in its entirety for all purposes.

STATEMENT OF GOVERNMENT INTEREST

The present invention was made in conjunction with Government funding under contract number FA8650-05-C-5425 awarded by the United States Air Force. The United States Government has certain rights in this invention.

FIELD OF THE INVENTION

The invention relates to non-linear optics, and more particularly to the production and use of birefringent crystals in nonlinear optical devices.

BACKGROUND OF THE INVENTION

Mid-infrared lasers are important for a growing number of applications, such as spectroscopy, remote chemical sensing, laser surgery, and infrared countermeasures. Typically, laser output at mid-infrared wavelengths is produced by using a nonlinear optical (NLO) crystal to shift the output wavelength of a solid state laser, such as a Nd:YAG (1.06-μm) laser or an erbium-doped fiber laser (1.55-μm), to a wavelength in the 2-12 μm range. Oxide-based crystals such as potassium titanyl phosphate, $KTiOPO_4$ (KTP), and periodically-poled lithium niobate, $LiNbO_3$ (PPLN) work well at the short end of this spectral range, but the output power from these materials falls off dramatically beyond 4 microns.

The I-III-$VI_2$ chalcopyrite crystals $AgGaS_2$ and $AgGaSe_2$ can be pumped at 1.06 μm and 1.55 μm respectively so as to generate output much deeper into the infrared (up to 12 μm), but they are plagued by low damage thresholds and extremely poor thermal properties that preclude their use for high average power applications. Crystals of $ZnGeP_2$, a II-IV-$V_2$ chalcopyrite, have significantly higher nonlinear coefficients and much better thermo-mechanical properties for high power operation, but they must be pumped by less common sources such as Tm- or Tm,Ho-lasers operating at wavelengths greater than 1.9 μm. Furthermore, the output power and efficiency of 2-micron-laser-pumped $ZnGeP_2$ optical parametric oscillators (OPOs) is limited by absorption losses at the pump wavelength.

II-IV-$V_2$ chalcopyrites like $ZnGeP_2$ are derived from III-V compound semiconductors (like GaP) by ordered substitution of group II (Zn) and group IV (Ge) atoms on the group III (Ga) site in the same way that I-III-$VI_2$ chalcopyrites like $AgGaS_2$ and $AgGaSe_2$ are derived from II-VI compound semiconductors (like ZnSe). While the I-III-$VI_2$ compounds offer low absorption losses, they are usually plagued by scattering losses due to precipitates which form on cooling as a result of off-stoichiometry congruent melting and retrograde solubility of the $III_2VI_3$-rich phase. They tend to have larger band gaps than their II-IV-$V_2$ counterparts, but are inferior in terms of hardness, thermal conductivity, anisotropic thermal expansion, and thermo-optic coefficients, all of which makes them prone to thermal lensing and laser-induced damage in both the surface and the bulk. They also have lower nonlinear coefficients than the II-IV-$V_2$ chalcopyrites.

The II-IV-$V_2$ compounds, therefore, offer superior properties in almost every respect. They are generally free of scattering centers, and absorption losses (at least in the phosphides) can be very low in the center of their transparency range. While they can be plagued by defect-related absorption losses near the band edge when grown from the melt, these losses can often be eliminated by post-growth processing.

Of course, not all II-IV-$V_2$ compounds are suitable for nonlinear optical applications. To be useful for nonlinear optical frequency conversion, a crystal must have sufficient birefringence for phase-matching. Because the speed of light (as determined by the refractive index, n) inside a crystal varies as a function of wavelength (a phenomenon known as "dispersion"), the input and output waves will normally remain in phase over a very short distance (~10-100 μm in the infrared), termed the "coherence length," beyond which frequency conversion ceases. A birefringent crystal exhibits two refractive indices: one for light polarized perpendicular to the optic axis (ordinary- or o-polarized) and another for light polarized parallel to the optic axis (extraordinary- or e-polarized). If the difference between the two refractive indices (i.e., the birefringence, $n_e - n_o$) exceeds the difference in refractive index at the two wavelengths (i.e., the dispersion), then a direction inside the crystal can be chosen such that input and output waves of opposite polarization can experience the same refractive index. Under these conditions, the two waves remain in phase (i.e. are "phase-matched"), allowing the frequency conversion process to build to reasonable efficiencies over a long interaction length.

In addition to phase matching, a nonlinear optical crystal must be highly transparent at the input and output wavelengths of interest, and it must have a band edge that is near or below one-half of the shortest wavelength involved in the frequency conversion process, so as to avoid two-photon absorption. For down-conversion processes such as optical parametric oscillation (OPO), optical parametric amplification (OPA), and difference frequency generation (DFG), the input wave represents the shortest wavelength, whereas for up-conversion processes such as second harmonic generation (SHG) or sum frequency generation (SFG) the shortest wavelength(s) is/are at the output. Pumping with a 1064 nm Nd:YAG solid state laser, for example, requires a band edge near or below 532 nm.

Finally, even if a candidate compound has adequate non-linearity, transparency, and phase-matching properties, it will not be possible to use the compound as the basis of an optical device unless a method is found for growing crystals of sufficient size and optical quality so that devices with the required crystallographic orientation can be fabricated. Oriented crystals with dimensions of at least 3 mm×3 mm×10 mm are typically required for practical devices, and the crystals must be free of cracks, twins, voids, inclusions, grain-boundaries, and other macroscopic defects, at least within the aperture and propagating path of the interacting waves.

Although at the time the present invention was made, $CdSiP_2$ was known to be a II-IV-$V_2$ chalcopyrite compound with at least some properties consistent with use in NLO devices, $CdSiP_2$ was not generally considered by those skilled in the art to be a likely candidate for practical NLO devices. The crystal structure of $CdSiP_2$ had been reported by S. C. Abrahams and J. L. Bernstein, *J. Chem. Phys.* Vol. 55, p. 796 (1971), incorporated herein by reference for all purposes. Specifically, Abrahams and Bernstein had reported that $CdSiP_2$ belongs to the tetragonal space group 42m, that its lattice parameters are respectively 5.68 A and 10.431 A for a and c, and Z=4 in each unit cell, and that the mass density of $CdSiP_2$ is 4.70 g/cm$^3$.

The birefringence of tiny 2×2×0.2 mm$^3$ $CdSiP_2$ crystals grown from a molten tin flux had been measured in the prior art and reported in N. Itoh, T. Fujinaga, and T. Nakau, "Birefringence in $CdSiP_2$," Jap. J. Appl. Phys. 17, 951-2, (1978) (incorporated herein by reference for all purposes) to be −0.045 at 840 nm, but no measurements were made in the infrared.

Several other optically relevant properties of $CdSiP_2$ were either uncertain or unknown at the time the present invention was made. For example, values reported in the prior art for the band gap of $CdSiP_2$ had ranged from 2.2 eV (563 nm) to 2.45 eV (506 nm), causing it to be unclear if $CdSiP_2$ would exhibit two-photon absorption if pumped by a pulsed 1064 nm laser. The long-wavelength transparency limit of $CdSiP_2$ had not been measured in the prior art. And while tiny samples (up to 5×2×1 mm$^3$) had been grown in the prior art by halogen-assisted vapor transport, as reported for example in E. Buehler and J. H. Wernick, *Journal of Crystal Growth* 8, 324 (1971), incorporated herein by reference for all purposes, the $CdSiP_2$ crystals produced thereby were far too small to be used for nonlinear optical devices. In fact, these prior art crystals were too small to enable measurement of the most relevant nonlinear optical properties, including the nonlinear coefficient, the transparency range, and the phase-matching characteristics. Furthermore, the methods used to grow these prior art crystals were not scalable to produce crystals having the required size and quality.

At the time the present invention was made, it therefore appeared doubtful to those of average skill in the art that $CdSiP_2$ crystals of optical device size and quality could be grown. Buehler and Wernick had reported an approximate melting point of 1120° C. for $CdSiP_2$ and a vapor pressure of 19.4 atm at 1100° C. (which extrapolates to 20.4 atm at 1120° C. and 23.9 atm at 1175° C.). The present inventors had even attempted to grow $CdSiP_2$ directly from a stoichiometric melt without success, finding that the quartz ampoules devitrified and reacted with $CdSiP_2$, and that the solidified melts were porous and polycrystalline. An equilibrium phase diagram for $CdSiP_2$ system had not been determined in the prior art, and it was not known if the compound would melt congruently, which is a necessary condition for melt growth.

A method was known in the prior art (see U.S. Pat. No. 5,611,856, incorporated herein in its entirety for all purposes) for producing single crystals of group II-IV-V$_2$ compounds of sufficient size and optical quality for use in NLO devices by pre-synthesizing the compound material from its constituents and separately melting and re-crystallizing by directional solidification in sealed quartz ampoules using a two-zone horizontal transparent furnace. Crystals with melting points as high as 1027° C. and vapor pressures as high as 7 atmospheres had been grown by this method. However, it did not appear at the time of the present invention that this method would tolerate the significantly higher temperatures (~1175° C. in the hot zone) and pressures (~24 atm) required to produce a $CdSiP_2$ crystal. In addition, it was not known whether the compound itself would melt congruently, and whether the quartz ampoules could be used without devitrifying or reacting with the compound. Finally, it was not apparent that a crystal of $CdSiP_2$ would be transparent and phase-matchable for mid-infrared frequency conversion, even if a crystal of sufficient size and quality could somehow be grown.

For all of these reasons, at the time the present invention was made $CdSiP_2$ was not generally considered by those skilled in the art to be a likely candidate crystal for practical NLO device applications.

A need exists, therefore, for $CdSiP_2$ single crystals of sufficient size and optical quality to be suitable for use in NLO devices, and for a method of producing such crystals. A need also exists for NLO devices that use such $CdSiP_2$ crystals to frequency-shift the output of 1.06 μm and 1.55 μm lasers to mid-infrared wavelengths ranging from 2-10 μm, and for frequency-shifting 2-μm lasers at high efficiencies and output powers into the 3-10 μm range. Furthermore, a need exists for a method of using such crystals of frequency-shifting the output of 1.06 μm, 1.55 μm, and 2-μm lasers to mid-infrared wavelengths ranging from 2-10 μm.

SUMMARY OF THE INVENTION

Large, high optical quality $CdSiP_2$ crystals suitable for use in nonlinear optical devices are claimed, as well as a method of producing such crystals by directional solidification from a stoichiometric melt. $CdSiP_2$ crystals of sufficient size and optical quality for use in NLO devices do not occur in nature, and could not be artificially produced before invention of the method claimed herein. The crystals of the present invention are therefore compositions of matter with essential differences in their properties as compared to naturally occurring and prior art manufactured crystals, wherein these essential differences include enhanced optical quality and size that enable the claimed crystals to be used as the basis of practical NLO devices, in contrast with $CdSiP_2$ crystals of the prior art that cannot be so used.

The claimed method of producing NLO-compatible $CdSiP_2$ crystals is similar to the prior art method of U.S. Pat. No. 5,611,856. However, it was unexpected at the time the present invention was made that large ingots of the compound $CdSiP_2$ could be successfully synthesized without explosion of the quartz ampoule due to the high temperatures and pressures required. Furthermore it was unexpected that large, high optical quality single crystals could be successfully grown in horizontal, transparent furnaces by directional solidification at the required temperatures and pressures.

Nonlinear optical devices are also claimed that use the $CdSiP_2$ crystals of the present invention to produce a shifted wavelength laser beam having a wavelength different from all incident beams. The claimed devices are capable of efficiently shifting laser wavelengths as short as 1 μm so as to produce electromagnetic radiation with wavelengths in the 2-10 μm wavelength range, and with average power levels in excess of 10 W, while avoiding severe thermal lensing due to the low absorption losses and high thermal conductivity of the claimed $CdSiP_2$ crystals.

One general aspect of the present invention is a nonlinear optical device comprising a negative uniaxial II-VI-V$_2$ crystal belonging to the space point group 42m and having NLO properties, whereby at least one incident beam of electromagnetic radiation can be directed into said crystal so as to generate electromagnetic radiation emerging from said crystal that includes at least one output wavelength different from the wavelengths of all incident beams of radiation, and wherein said crystal is a single crystal of $CdSiP_2$. In various embodiments, the $CdSiP_2$ crystal includes an input surface capable of receiving the at least one incident beam of electromagnetic radiation and an output surface capable of transmitting an emerging beam of electromagnetic radiation.

In some embodiments, the single crystal of $CdSiP_2$ is oriented relative to polarization and propagation directions of the incident radiation so as to allow phase-matched propagation of the incident and emerging radiation. And in certain embodiments, the single crystal of $CdSiP_2$ has a total volume of at least 20 mm$^3$.

In various embodiments, the single crystal of $CdSiP_2$ is free of cracks, twins, voids, inclusions, grain-boundaries, and all other macroscopic defects throughout all apertures and propagating paths of all electromagnetic waves interacting therein. In certain embodiments all of the incident beams of electromagnetic radiation have wavelengths that fall in the range 0.5 μm to 10 μm, and in other embodiments the electromagnetic radiation emerging from said crystal includes at least one output wavelength that falls in the range 0.5 μm to 10 μm. Some embodiments are configured for transmitting an emerging beam having an average power of at least 10 Watts.

Various embodiments further include an input coupler configured to enable the incident beams of electromagnetic radiation to be directed into the nonlinear optical crystal, and an output coupler configured to enable extraction of at least one emerging beam of electromagnetic radiation from the nonlinear optical crystal.

In some embodiments, the output coupler includes an optical filter configured to isolate the emerging beam from other beams of electromagnetic radiation. Certain embodiments further include an orientation adjustment mechanism configured to adjust an orientation of the nonlinear optical crystal relative to directions of propagation and polarization of the incident beam or beams. Other embodiments further include a temperature adjusting mechanism configured to adjust a temperature of the nonlinear optical crystal.

In certain embodiments the input coupler includes an input mirror that is at least partially transmissive of the incident beam or beams, and the output coupler includes an output mirror that is at least partially transmissive of the emerging beam.

In some embodiments the $CdSiP_2$ single crystal is grown from a compound produced by a two-temperature method comprising vacuum sealing Cd, Si, and P in an ampoule in a molar ratio of nominally 1:1:2, not including any excess quantities added so as to account for a vapor phase above a melt, the Cd and Si being physically mixed at a first end of the ampoule and the P being located at a second end of the ampoule, and heating the Cd and Si at least near the melting point of the compound $CdSiP_2$ while heating the P to a lower temperature sufficient to cause the P to volatilize and react with the molten Cd and Si, thereby forming $CdSiP_2$ compound. And in some embodiments the $CdSiP_2$ single crystal is grown by directional solidification from a stoichiometric melt containing Cd, Si, and P in a molar ratio of nominally 1:1:2.

In various embodiments the nonlinear optical device is configured for frequency conversion by means of phase-matched sum frequency generation, second harmonic generation, phase-matched difference frequency generation, phase-matched optical parametric generation, phase-matched optical parametric amplification, and/or phase-matched optical parametric oscillation.

In some embodiments, the electromagnetic radiation emerging from the $CdSiP_2$ single crystal includes at least one output wavelength of substantially about 6.45 μm. In certain embodiments the nonlinear optical device is configured for non-critical phase matching and the electromagnetic radiation emerging from said crystal is temperature tuned so as to include a wavelength of substantially about 6.45 μm. And in various embodiments the nonlinear optical device is pumped by a solid-state laser having an output wavelength of 1064 nm.

Another general aspect of the present invention is an infrared laser surgery scalpel. The infrared laser surgery scalpel includes a single crystal of $CdSiP_2$ having NLO properties, into which at least one incident beam of electromagnetic radiation can be directed so as to generate electromagnetic radiation emerging from the crystal that includes an output wavelength of substantially about 6.45 μm. In some embodiments the at least one incident beam is a single incident beam produced by a solid-state laser having a wavelength of substantially about 1064 nm. And in certain embodiments the nonlinear optical device is configured for non-critical phase matching and the electromagnetic radiation emerging from the crystal is temperature tuned so as to include a wavelength of substantially about 6.45 μm.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and not to limit the scope of the inventive subject matter.

DETAILED DESCRIPTION

Figure 1A:
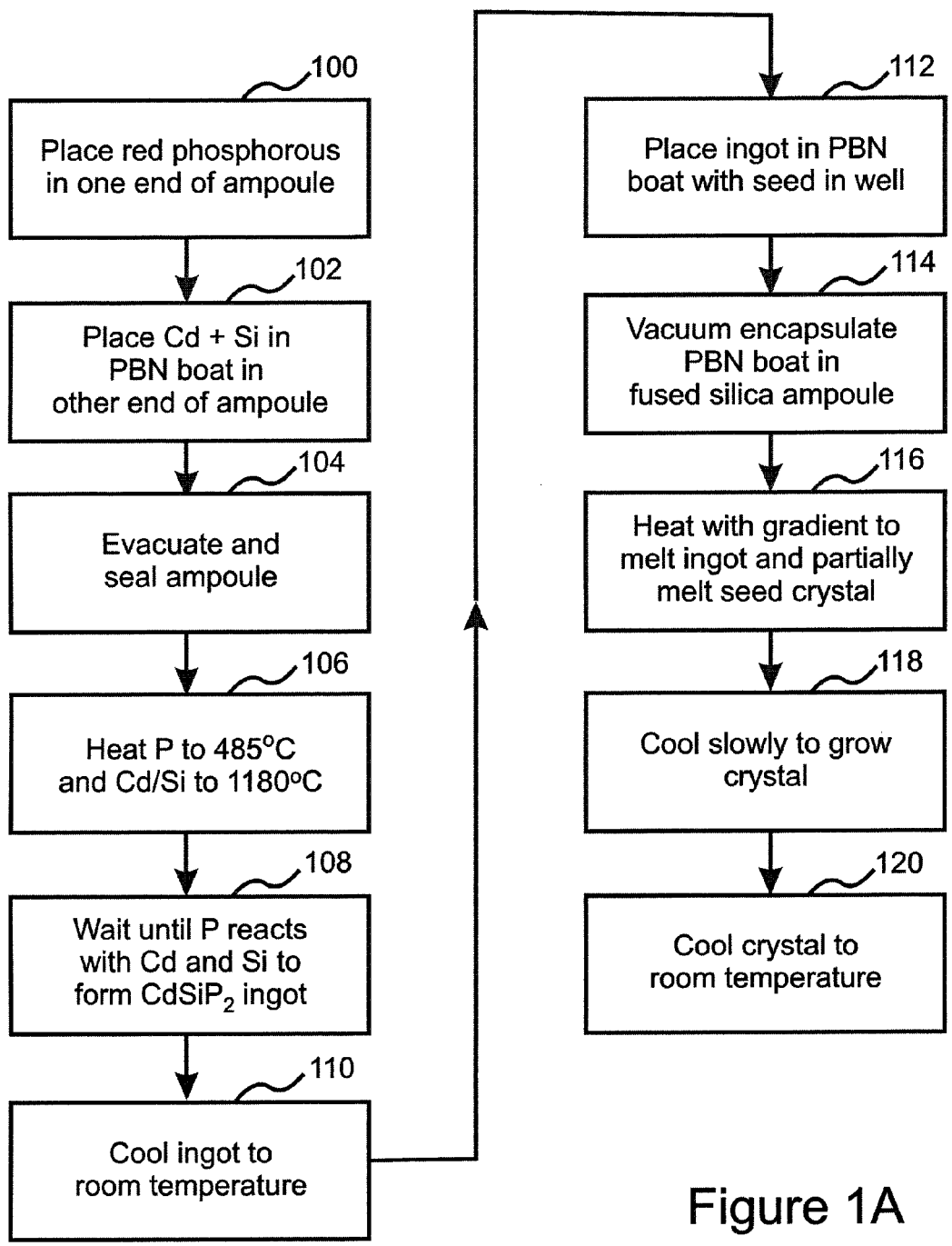
FIG. 1A is a flow diagram that illustrates the method of the present invention for producing $CdSiP_2$ crystals suitable for use in NLO devices.

With reference to FIG. 1A, the method of the present invention for producing a single crystal of $CdSiP_2$ suitable for use in NLO devices includes the following steps:

a) placing red phosphorus (P) at one end of a quartz ampoule 100 and a PBN or PBN-coated graphite boat containing cadmium (Cd) and silicon (Si) at the other end 102 of the ampoule in a molar ratio of Cd:Si:P=1:1:2, and evacuating and sealing the ampoule 104;

b) heating the sealed ampoule in a two-zone furnace so that the P end of the furnace is maintained at a cold zone temperature of 485° C. and the Cd and Si end of the furnace is maintained at a hot zone temperature of 1180° C. 106 and waiting until the P fully transports and reacts with Cd and Si to form $CdSiP_2$ (4-24 hours) 108 and then cooling to room temperature 110;

c) loading the resulting synthesized $CdSiP_2$ ingot into a PBN or PBN-coated graphite boat fitted with a well containing a seed crystal 112, and vacuum-encapsulating the boat in a fused silica ampoule 114;

d) heating the encapsulated PBN or PBN-coated graphite boat in a furnace with an axial gradient of 1-5° C./cm to about 1130° C. and adjusting the temperature so as to fully melt the CdSiP$_2$ ingot and partially melt the seed crystal 116;

e) cooling the encapsulated PBN or PBN-coated graphite boat at a rate of between 0.02° C. per hour and 1° C. per hour so as to achieve directional solidification of the CdSiP$_2$ at a crystal growth rate of 0.2 to 2 mm/hour 118; and f) cooling the resultant CdSiP$_2$ crystal to room temperature at a rate of between 5° C./hour and 100° C./hour 120.

Figure 1B:
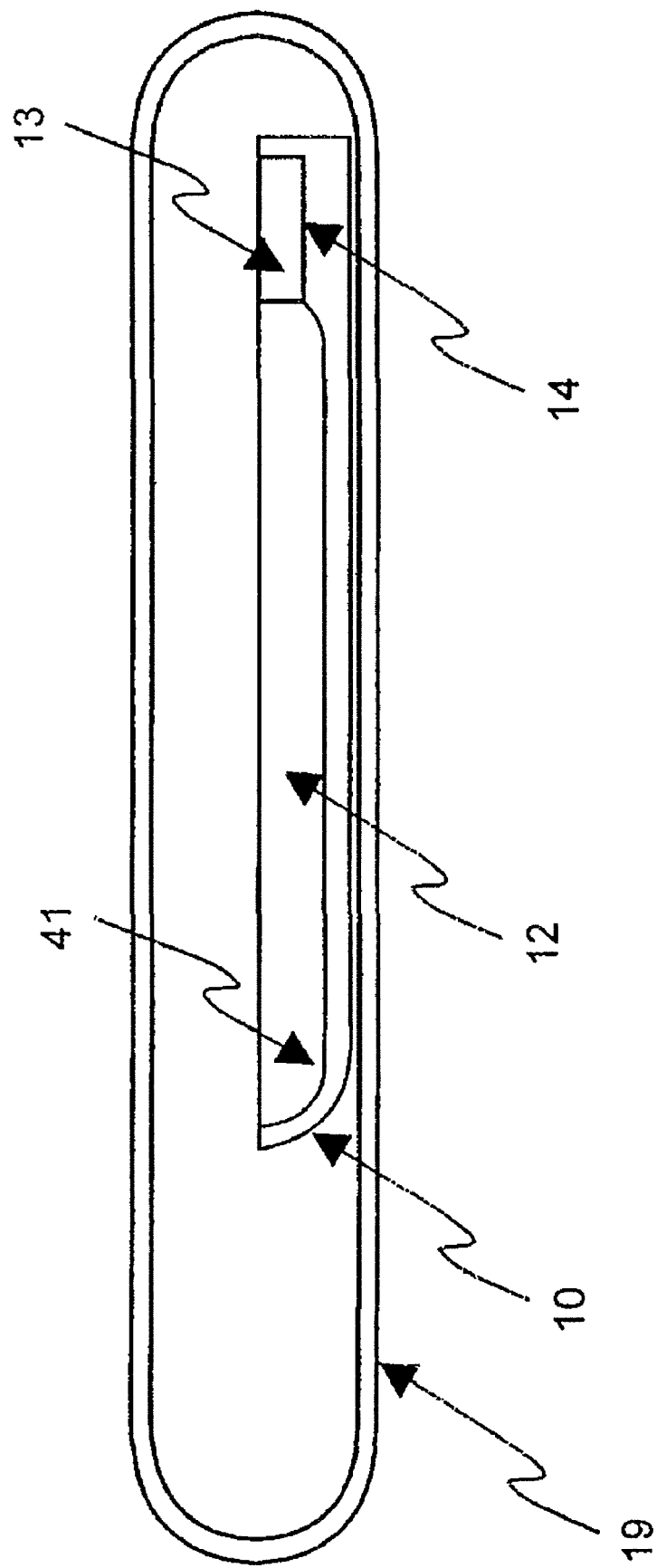
FIG. 1B is a sectional side view showing the configuration of a boat and ampoule used for crystal growth in an embodiment of the present invention.

FIG. 1B illustrates a PBN-coated graphite boat 10 of a preferred embodiment, the boat being fitted with a well 14 containing a seed crystal 13, and being vacuum-encapsulated within a fused silica ampoule 19. A single crystal seed 13, which should be free of cracks, twins, and secondary grains, is placed in the seed well 14 of the boat 10. The seed crystal 13 can be of random orientation, or can be oriented along a high symmetry direction of the crystal such as [100], [001], [110], [112], etc. In various embodiments, the seed crystal is oriented along the phase-matching direction required for a specific laser application.

Figure 1C:
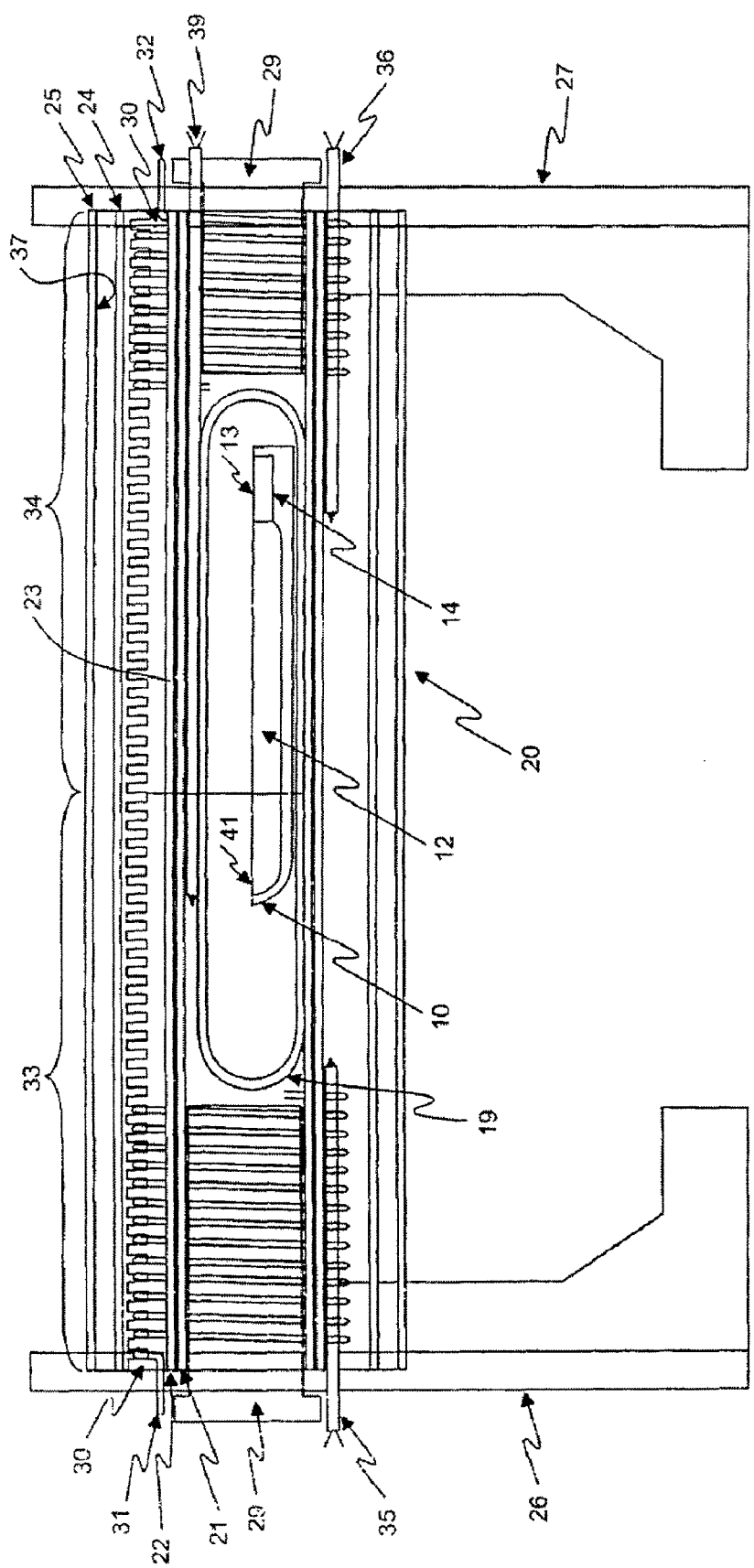
FIG. 1C is a sectional side view of a transparent furnace used for crystal growth in an embodiment of the present invention.

FIG. 1C illustrates a dual zone, horizontal temperature gradient or gradient freeze furnace 20 used in an embodiment of the present invention to heat the encapsulated graphite boat with an axial gradient of 1-5° C./cm to about 1130° C. and adjust the temperature so as to fully melt the CdSiP$_2$ ingot and partially melt the seed crystal. Furnace 20 generally consists of four concentric cylinders, including an inner cylinder 21 known as the muffle tube, a two-piece heater support tube 22, 23 a shield tube 24, and an outer gold-coated tube 25 known as the mirror tube. Cylinders 21-25 are closed and supported by ceramic end caps 26, 27. The muffle tube 21 supports the ampoule 19 near the concentric radial center of all the cylinders 21-25. With ampoule 19 located within cylinder 21, the ends thereof are closed with insulation 29. Heating coils 31, 32 are helically wound onto heater support tubes 22 and 23 and create separate heating zones 33, 34 in their respective halves. The heating coil spacing is selected to yield a desired range of longitudinal temperature gradients.

Figure 4:
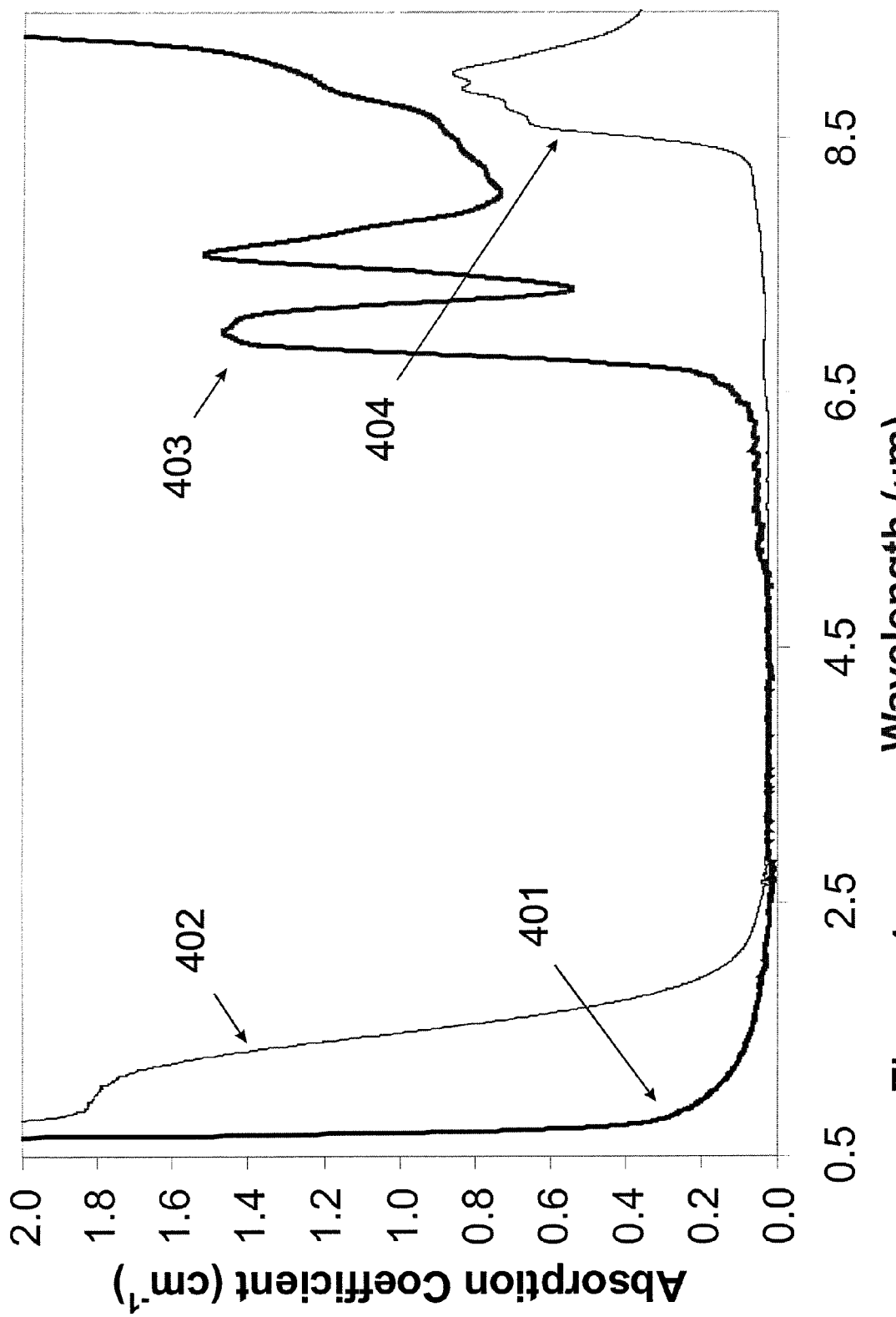
FIG. 4 is a plot of absorption coefficient vs. wavelength comparing the transparency range of $CdSiP_2$ crystals of the present invention with that of $ZnGeP_2$, another nonlinear optical crystal of the prior art, illustrating the much lower losses of the $CdSiP_2$ crystals in the 0.5-2 μm wavelength range.

The method described above has been used to produce single crystals of CdSiP$_2$ suitable for use in NLO devices with diameters up to 19 mm or more and lengths up to several centimeters. These crystals of the present invention have been used to measure the following NLO properties:

1. Wide Wavelength Transparency Range:

The inventors of the present invention have examined the transmission characteristics of CdSiP$_2$ single crystals produced using the method disclosed above, and have found that the CdSiP$_2$ single crystals are transparent in the wavelength range of 500 nm to 9500 nm. The measured transparency range of a CdSiP$_2$ crystal of the present invention, plotted as absorption coefficient versus wavelength, is shown in FIG. 4. The thick line 401, 403 indicates the measured absorption spectrum for CdSiP$_2$, whereas the thin line 402, 404 indicates the measured absorption spectrum for a nonlinear optical crystal of the prior art, ZnGeP$_2$. Note that the absorption losses between the band edge and 2 μm 401 are substantially lower in a CdSiP$_2$ crystal of the present invention than in the prior art ZnGeP$_2$ crystal 402, allowing CdSiP$_2$ crystals to be pumped by 1 μm and 1.55 μm lasers, which are processes not phase-matchable using the prior art crystal ZnGeP$_2$.

In addition, CdSiP$_2$ crystals of the present invention exhibit a 2 μm absorption coefficient up to 20 times lower than that ZnGeP$_2$, making CdSiP$_2$ a promising alternative to ZnGeP$_2$ for powerful and efficient mid-infrared OPOs pumped by Tm and Ho lasers. The onset of multi-phonon absorption in a CdSiP$_2$ crystal of the present invention, with peaks at 7 μm and 7.6 μm 403, occurs at shorter wavelengths than in the prior art ZnGeP$_2$ crystal, which has a peak at 9 μm 404. This limits the usefulness of CdSiP$_2$ crystals for frequency conversion processes involving wavelengths beyond 6.7 μm.

2. Large Nonlinear Coefficient:

The inventors have measured the nonlinear coefficient of a CdSiP$_2$ single crystal produced using the method disclosed above, and have obtained a value of 84.5 pm/V, which is 2.56 times that of AgGaSe$_2$ (33 pm/V) and 7 times larger than that of AgGaS$_2$ (12 pm/V). This was an unexpectedly high value for the nonlinear optical coefficient, since plotting the nonlinear coefficients of other II-VI-V$_2$ chalcopyrites as a function of band gap predicted a value closer to 53 pm/V. This measured value of 84.5 pm/V is, in fact, the highest nonlinear optical coefficient of any known phase-matchable nonlinear optical crystal that can be pumped by a solid state laser.

3. High Thermal Conductivity:

The inventors have measured the thermal conductivity of an 8 mm×8 mm×1.97 mm CdSiP$_2$ sample using a NETZSCH LFA 447 Nanoflash instrument. The sample faces were coated with gold (~0.1 μm) and carbon paint (~5 μm) to block any transmitted light. Room-temperature (25° C.) measurements of thermal diffusivity, heat capacity, and thermal conductivity yielded values of 7.69 mm$^2$/s, 0.446 J/g/K, and 13.6 W/mK respectively. This thermal conductivity value is an order of magnitude higher than that of the prior art NLO crystals AgGaS$_2$ (1.4 W/mK) and AgGaSe$_2$ (1.0 W/mK) used in the prior art for shifting 1.06-μm and 1.55-μlm lasers into the mid-IR. This high thermal conductivity, coupled with the low absorption losses illustrated in FIG. 4, enables the generation of mid-infrared laser radiation in excess of 10 W.

4. Refractive Indices and Phase Matching Conditions:

Employing the method of prism minimum deviation, the inventors of the present invention also measured the principal refractive indices of CdSiP$_2$. Using the least square fitting method, the Sellmeier equations were obtained as follows:

$$n_o^2 = 2.931 + \frac{6.4248 * \lambda^2}{\lambda^2 - 0.10452} - 0.0034888 * \lambda^2 \qquad (1)$$

and $$n_e^2 = 3.4975 + \frac{5.5451 * \lambda^2}{\lambda^2 - 0.11609} - 0.0034264 * \lambda^2 \qquad (2)$$

The refractive index data revealed that CdSiP$_2$ is a negative uniaxial crystal ($n_e - n_o < 0$) with a birefringence in the mid-infrared around −0.05). The Sellmeier equations above were used to calculate the phase matching conditions for CdSiP$_2$ crystals pumped at various laser wavelengths.

Figure 2:
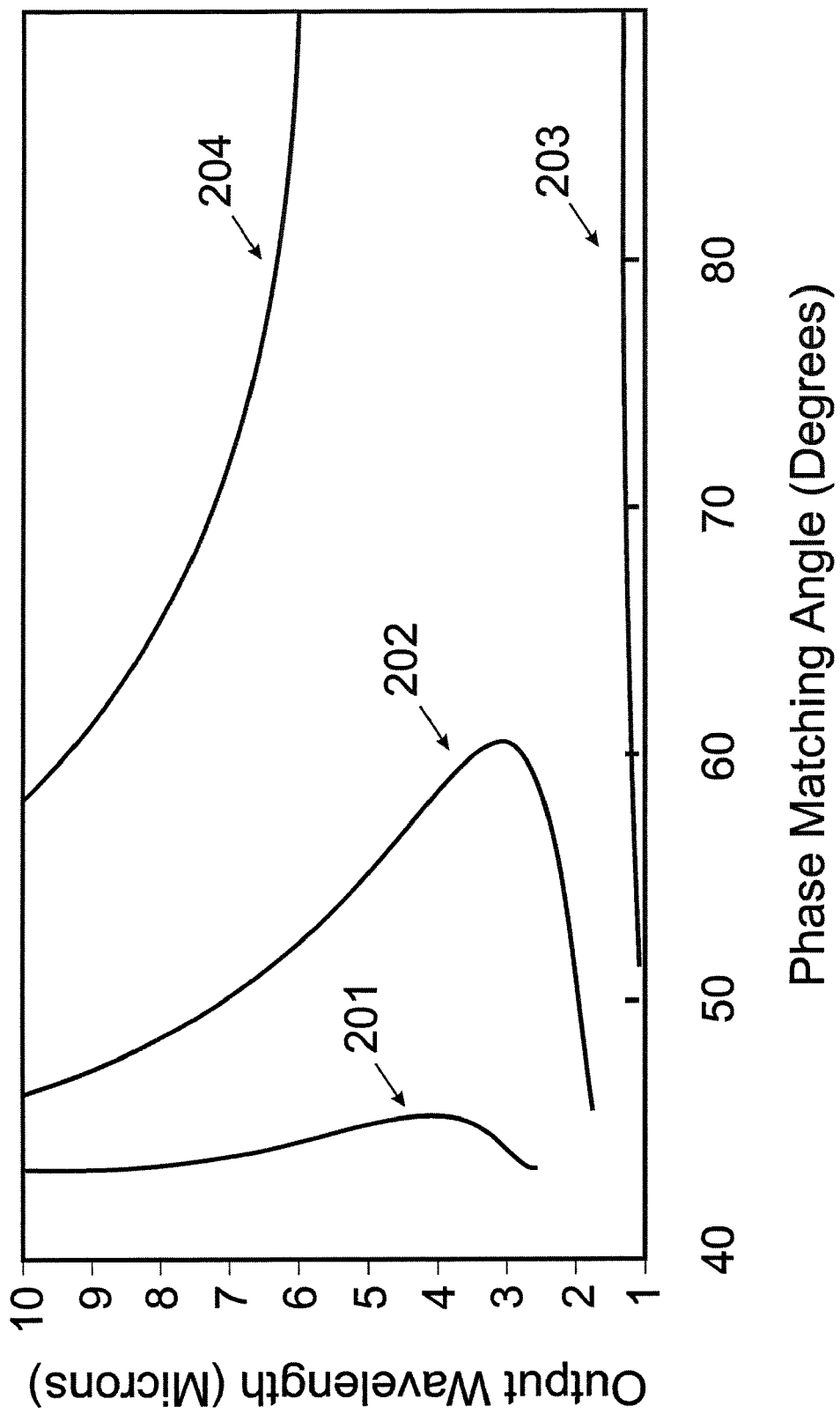
FIG. 2 is a graph of the type I phase matching curves for $CdSiP_2$ crystals of the present invention pumped at laser wavelengths of 2055 nm (1), 1550 nm (2), and 1064 nm (3,4)

FIG. 2 shows the Type I phase matching curves for CdSiP$_2$ crystals pumped at laser wavelengths of 2055 nm (201), 1550 nm (202), and 1064 nm (203, 204). While curves are presented for these pumping wavelengths as examples and as indicative of embodiments of the present invention, it will be understood that the invention is not limited to lasers operating with the pumping wavelengths illustrated in FIG. 2, nor is the present invention limited to type I interactions. At each phase matching angle, two output wavelengths are generated, an output with a wavelength that is less than or equal to twice the pump wavelength, termed the "signal" wave, and an output with a wavelength greater than or equal to twice the pump wavelength, termed the "idler" wave.

According to FIG. 2, pumping a CdSiP$_2$ NLO device with a 2055 nm laser (curve 201) at internal phase matching angles between 43 and 45 degrees relative to the c-axis (optic axis)

will generate output wavelengths between 2.6 µm and 9.31 µm. Pumping with a 1550 nm laser (curve 202) at internal phase matching angles between 45.5 and 60.5 degrees relative to the c-axis (optic axis) will generate output wavelengths from 1.71 µm to greater than 10.5 µm. And pumping with a 1064 nm laser at internal phase matching angles between 50 and 90 degrees relative to the c-axis (optic axis) will generate signal output wavelengths from 1.1 µm to 1.3 µm (curve 203) and idler output wavelengths from 6 µm to greater than 10.5 µm (curve 204). Although 1064 nm pumping is unable to access the 1.3 µm to 6 µm range, $CdSiP_2$ does allow non-critically phase matched output (i.e. 90-degree phase-matching with no walk-off) around 6.2 µm, which would be advantageous for medical applications in this range.

5. Temperature-Tunable Devices

The present inventors also measured the change in the ordinary and extra-ordinary refractive indices, and the consequent change in the corresponding Sellmeier equations, as a function of temperature. The resulting temperature-dependent Sellmeier coefficients are listed below in Table 1, and indicate that the $CdSiP_2$ crystals of the present invention are more temperature-tunable than most other nonlinear optical chalcopyrite crystals known in the prior art. The data indicate, for example, that a 2-µm pumped OPO based on $CdSiP_2$ can be tuned in wavelength between 3.4 and 4.8 µm by varying the temperature of the $CdSiP_2$ crystal between 10° C. and 70° C. Likewise, a 1.064-µm-pumped Type I $CdSiP_2$ OPO will produce non-critically phase-matched output at 6.18 µm at 25° C., but can be temperature tuned to produce non-critically phase-matched output at 6.45 µm at 99° C. (a modest temperature increase that can easily be achieved in practical hardware). The ability to efficiently directly generate 6.45 µm radiation from a 1.064 µm-pumped non-critically phase-matched OPO is valuable for laser surgery applications.

TABLE 1

|   | $n_o$ | $n_e$ |
|---|---|---|
| A | $3.0449 + 1.214 \times 10^{-4} T(K)$ | $3.3978 + 1.224 \times 10^{-4} T(K)$ |
| B | $6.1164 + 5.459 \times 10^{-4} T$ | $5.4297 + 6.174 \times 10^{-4} T(K)$ |
| C | 0.0034888 | 0.0034264 |
| D | 0.10452 | 0.11609 |

$CdSiP_2$ o- and e-polarized temperature-dependent Sellmeier coefficients, where $n^2 = A + B\lambda^2/(\lambda^2 - D) - C\lambda^2$.

Figure 3:
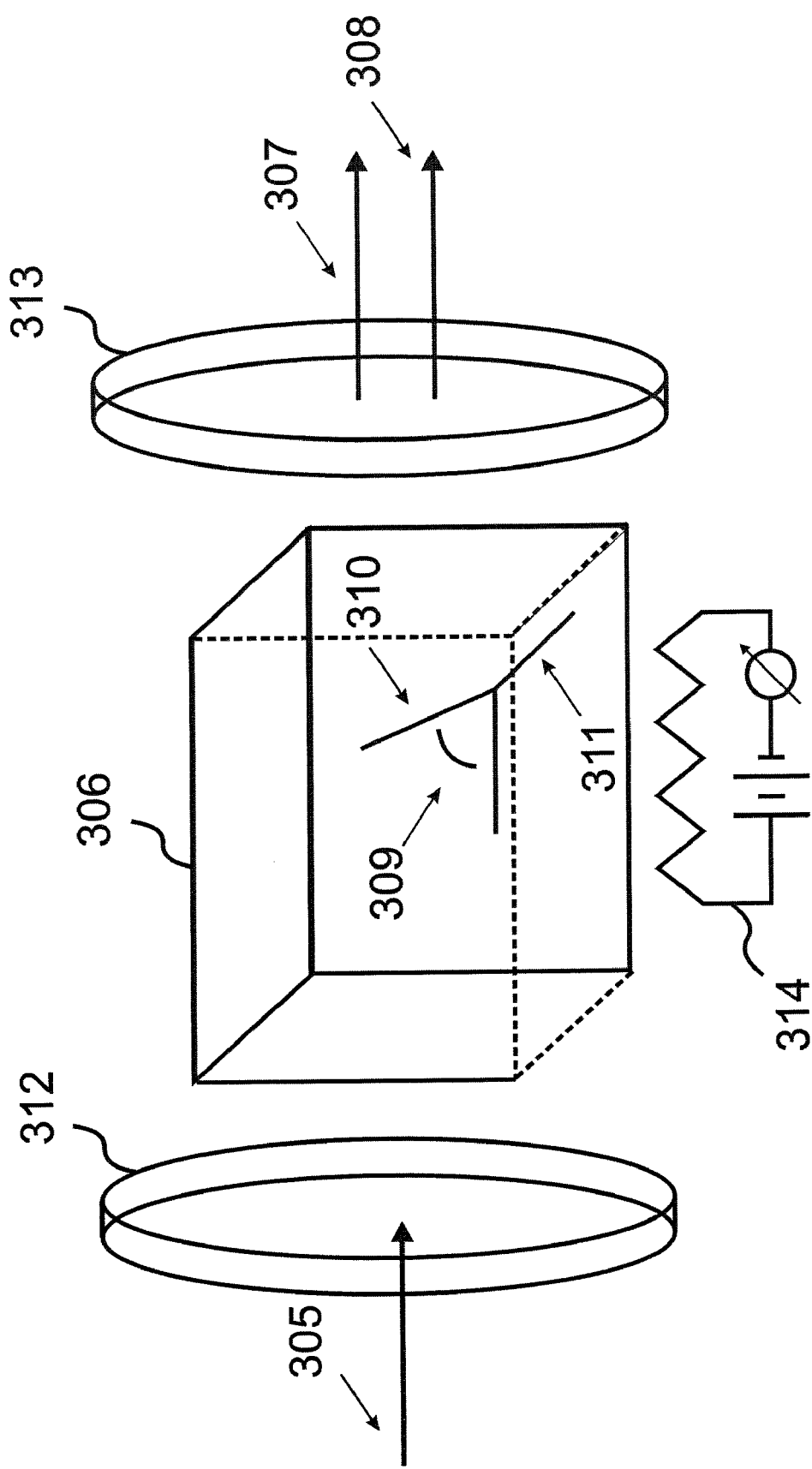
FIG. 3 is a functional diagram of an embodiment of the NLO device of the present invention.

FIG. 3 is a functional illustration of an embodiment of an NLO device made of a single crystal of $CdSiP_2$ of the present invention. The input or pump wave 305 is incident on the $CdSiP_2$ NLO crystal 306 and generates signal 307 and idler 308 output waves. The crystal is cut so that wave 305 entering the crystal 306 will propagate through the crystal 306 at a phase matching angle 309 relative to the c-axis 310. The wavelengths of the signal wave 307 and idler wave 308 can be tuned by varying the phase matching angle 309 by rotating the crystal 6 about the tuning axis 311. This conversion process is called optical parametric generation ("OPG") if no mirrors are used to resonate the output wavelengths, and is called optical parametric oscillation ("OPO") if the embodiment includes an input mirror 312 which is highly transmissive at the pump wavelength and highly reflective at the signal wavelength and/or the idler wavelength, and an output coupler 313 which is highly transmissive at the pump wavelength and partially reflective at the signal wavelength and/or the idler wavelength. A crystal heater 314 can be used to temperature-tune the output wavelength of the nonlinear optical device, particularly in the case of a non-critically phase-matched OPO. Other NLO conversion processes such as difference frequency generation ("DFG"), sum frequency generation ("SFG"), and second harmonic generation ("SHG") can also be performed with $CdSiP_2$ crystals of the present invention.

In various embodiments the polarizations of the interacting waves and the crystallographic orientation of the optic axis 310 and tuning axis 311 are chosen so as to satisfy the conditions for a given phase matching type (type I, type II, etc.) and so as to maximize the efficiency of the frequency conversion process using the principles detailed for example in M. J. Weber (ed.) *CRC Handbook of Laser Science and Technology*, Vol. 3., (CRC Press, Boca Raton, Fla., 1986), relevant portions incorporated by reference for all purposes.

One example of a device according to FIG. 3 is a medical laser scalpel. The device is pumped by a conventional laser such as a Nd:YAG laser at 1.06 µm and produces an output laser beam of approximately 6.45 µm, which is a wavelength with high soft tissue absorbance and cutting efficiency. In various embodiments of this device, the $CdSiP_2$ crystal 306 is oriented for noncritical phase matching with no "walk-off" of the emerging beam relative to the incident beam. The crystal 306 is heated by the heater 314 to a temperature of approximately 100° C., so as to tune the output wavelength to approximately 6.45 µm. A specific medical laser scalpel embodiment is discussed in more detail in Example 3 below.

It can be seen from the discussion above that the claimed single crystals of $CdSiP_2$ are novel NLO crystals having excellent NLO properties. The claimed NLO devices made using the claimed $CdSiP_2$ crystals have superior properties as compared to prior art NLO devices made using either $AgGaSe_2$ or $AgGaSe_2$ crystals. In particular, the claimed devices have a higher nonlinear coefficient and higher thermal conductivity than these prior art devices, making them more attractive for high average power laser frequency conversion in the mid-infrared.

Example 1

22.0453 g of red phosphorus was loaded into one end of a heavy-walled, fused silica ampoule, and a PBN-coated graphite boat containing 9.9948 g silicon and 40.0034 g cadmium was loaded into the opposite end. The ampoule was evacuated, sealed, and loaded into a two-zone shunt-type tube furnace with a Hastelloy C-276 protective liner. The programmed heating cycle was as follows: zone 1 (hot zone, containing the boat with Cd and Si) was heated at 50° C./hr to 1025° C., 37.9-hr soak, 25° C./hr to 1180° C., 8-hr soak, cool at 100° C./hr; zone 2 (containing P) was heated at 50° C./hr to 485° C., 28-hr soak, 25° C./hr to 1180° C., 8-hr soak, cool at 100° C./hr.

The resulting single phase polycrystalline ingot was loaded into a PBN-coated graphite boat with a seed well containing a $CdSiP_2$ single crystal seed oriented for horizontal growth along the (001) c-axis direction with the (110) axis normal to the top surface. The boat, charge, and seed were vacuum encapsulated in a heavy-walled, fused silica ampoule and heated in a two-zone transparent furnace at 16.7° C./hour to set points of 1125° C. and 1115° C. respectively to establish an axial temperature gradient of 1.5° C./cm. The set points were gradually raised to 1130° C. and 1120° C. to partially melt the seed crystal, followed by cooling at 0.15° C./hr for 160 hours to induce directional solidification at a rate of 1 mm/hour. Once fully solidified, the crystal was cooled at 5° C./hour to room temperature. The resulting "D"-shaped crystal was 19 mm wide, 10 mm high and 140 mm long: the first 15 mm of growth were a clear, crack-free, single crystal grain that reproduced the orientation of the seed crystal.

Example 2

A $CdSiP_2$ crystal obtained by using the procedure of Example 1 with excellent mechanical properties was cut and polished into a body of $3\times6\times12$ mm$^3$ after determination of the crystallographic axes a and c at phase matching angles of $\theta_m$=42.5 degrees and $\phi$=45 degrees. The crystal was placed in the optical path shown in FIG. 3 without mirrors 312 and 313. The incident wave 305 was from a frequency-doubled, Q-switched $CO_2$ laser of wavelength 4.64 microns. The emerging second harmonic wave 307, 308 with a wavelength of 2.32 microns was obtained. The uncoated crystal achieved 30% optical-to-optical conversion efficiency.

Example 3

A $CdSiP_2$ crystal obtained by using the procedure of Example 1 was cut into a body of $6\times6.75\times9.5$ mm$^3$ after determination of the crystallographic axes a and c at phase matching angles of $\theta_m$=90 degrees and $\phi$=45 degrees. The residual losses measured for the relevant polarizations (e for the pump and o for the signal and idler) were 0.185 cm$^{-1}$ at 1064 nm, 0.114 cm$^{-1}$ near 1.3 µm, and 0.014 cm$^{-1}$ near 6.4 µm. Both faces were AR-coated for the three wavelengths (pump, signal, and idler) and the 8-layer coating resulted in averaged reflectivity per surface of ~0.35% at 1064 nm, ~0.4% at 1275 nm and ~0.8% at 6400 nm. The crystal was placed in the optical path shown in FIG. 3. The incident wave 305 was from a Q-switched 1064 nm Nd:YAG laser: no two-photon absorption was observed. The internal crystal angle was approximately 0.67° below the desired 90° interaction angle, resulting in a signal wavelength 307 of 1.277 µm and an idler wavelength 308 of 6.398 µm, which was increased to 6.45 µm by heating the crystal 306 using a heater 314. This interaction is extremely useful for laser surgery applications at 6.45 µm, including minimally-invasive neurosurgery. An extremely effective laser scalpel for cutting soft tissue has been demonstrated at this wavelength using a free electron laser (see Nature 371, 416-419, 29 Sep. 1994, incorporated herein in its entirety for all purposes), which is an enormous and extremely expensive laser source. The $CdSiP_2$ crystal of the present invention will allow direct, efficient, non-critically phase-matched generation of the desired wavelength from a compact, powerful, and readily available Nd:YAG pump laser.

The foregoing description of the embodiments of the invention has been presented for the purposes of illustration and description. It is not intended to be exhaustive or to limit the invention to the precise form disclosed. Many modifications and variations are possible in light of this disclosure. It is intended that the scope of the invention be limited not by this detailed description, but rather by the claims appended hereto.

What is claimed is:

1. A nonlinear optical device comprising a single crystal of $CdSiP_2$ having NLO properties, said single crystal having a cut and polished incident face and a cut and polished emergent face, whereby at least one incident beam of electromagnetic radiation can be directed into said incident face so as to generate electromagnetic radiation emerging from said emergent face that includes at least one output beam wavelength different from the wavelengths of all incident beams of radiation, and wherein all of said incident and output beams have wavelengths between 0.5 µm and 10 µm.

2. The nonlinear optical device of claim 1, wherein the single crystal of $CdSiP_2$ is oriented relative to polarization and propagation directions of the incident radiation so as to allow phase-matched propagation of the incident and emerging radiation.

3. The nonlinear optical device of claim 1, wherein the single crystal of $CdSiP_2$ has a total volume of at least 20 mm$^3$.

4. The nonlinear optical device of claim 1, wherein the single crystal of $CdSiP_2$ is free of cracks, twins, voids, inclusions, grain-boundaries, and all other macroscopic defects throughout all apertures and propagating paths of all electromagnetic waves interacting therein.

5. The nonlinear optical device of claim 1, wherein the electromagnetic radiation emerging from said crystal includes at least one output wavelength that falls in the range 0.5 µm to 10 µm.

6. The nonlinear optical device of claim 1, wherein the nonlinear optical device is configured for frequency conversion by means of phase-matched sum frequency generation.

7. The nonlinear optical device of claim 1, wherein the nonlinear optical device is configured for frequency conversion by means of second harmonic generation.

8. The nonlinear optical device of claim 1, wherein the nonlinear optical device is configured for frequency conversion by means of phase-matched difference frequency generation.

9. The nonlinear optical device of claim 1, wherein the nonlinear optical device is configured for frequency conversion by means of phase-matched optical parametric generation.

10. The nonlinear optical device of claim 1, wherein the nonlinear optical device is configured for frequency conversion by means of phase-matched optical parametric amplification.

11. The nonlinear optical device of claim 1, wherein the nonlinear optical device is configured for frequency conversion by means of phase-matched optical parametric oscillation.

12. The nonlinear optical device of claim 1, wherein the electromagnetic radiation emerging from said crystal includes at least one output wavelength of substantially about 6.45 µm.

13. The nonlinear optical device of claim 1, wherein the nonlinear optical device is configured for non-critical phase matching and the electromagnetic radiation emerging from said crystal is temperature tuned so as to include a wavelength of substantially about 6.45 µm.

14. The nonlinear optical device of claim 1, wherein the nonlinear optical device is pumped by a solid-state laser having an output wavelength of 1064 nm.

15. The nonlinear optical device of claim 1, wherein the incident and output beams include a first beam having a wavelength between 1.06 µm and 2 µm and a second beam having a wavelength between 2 µm and 10 µm.

* * * * *